United States Patent [19]

Vedamuthu

[11] 3,975,545

[45] Aug. 17, 1976

[54] STABILIZING AGENTS FOR FROZEN LACTIC ACID PRODUCING BACTERIA COMPOSITIONS

[75] Inventor: Ebenezer R. Vedamuthu, Bradenton, Fla.

[73] Assignee: Microlife Technics, Inc., Sarasota, Fla.

[22] Filed: June 16, 1975

[21] Appl. No.: 586,943

[52] U.S. Cl. .................................. 426/40; 426/42; 426/43; 426/61; 195/75
[51] Int. Cl.² .................... A23C 9/12; A23C 19/02
[58] Field of Search .................... 426/34, 40, 61, 42, 426/43; 195/59, 75, 96

[56] References Cited
UNITED STATES PATENTS

| | | | |
|---|---|---|---|
| 2,518,355 | 8/1950 | Mejlho | 195/59 |
| 3,404,984 | 10/1968 | Olsen | 195/96 |
| R28,488 | 7/1975 | Farr | 195/59 |

*Primary Examiner*—A. Louis Monacell
*Assistant Examiner*—R. A. Yoncoskie
*Attorney, Agent, or Firm*—Miller, Morriss, Pappas & McLeod

[57] ABSTRACT

Frozen compositions of lactic acid producing bacteria which incorporate an alkali metal salt of glycerophosphoric acid are described. These salts reduce damage to the bacteria upon freezing and storage which with certain bacteria is evidenced by enhanced lactic acid forming activity upon thawing and use of the compositions as fermented dairy product starter cultures.

19 Claims, No Drawings

STABILIZING AGENTS FOR FROZEN LACTIC ACID PRODUCING BACTERIA COMPOSITIONS

SUMMARY OF THE INVENTION

The present invention relates to freezing stabilized lactic acid forming bacterial compositions. The present invention particularly relates to frozen compositions incorporating certain alkali metal salts of glycerophosphoric acid for this purpose.

The freezing stabilization of bacterial concentrates of lactic acid producing bacteria to maintain their viability over long periods of time is well known in the prior art. Such compositions are particularly described in U.S. Reissue Pat. No. 28,276. In this patent, the use of glycerol as a stabilizing agent is described.

Glycerol is a very effective freezing stabilizing agent; however, there is some cell damage resulting from freezing of the bacterial concentrates. The damage can be evidenced by inhibited or retarded lactic acid producing properties of the concentrates during the initial periods of fermentation upon thawing and use in the production of fermented dairy products as compared to fresh, unfrozen concentrates.

It is therefore an object of the present invention to provide frozen bacterial compositions containing new stabilizing agents which exhibit reduced cell damage because of the freezing and in certain instances improved lactic acid producing properties. These and other objects will become increasingly apparent by reference to the following description.

DETAILED DESCRIPTION OF THE INVENTION

The present invention relates to a frozen bacterial composition comprising live bacterial cells of the kind which form lactic acid in milk mixed with a cell growth medium and containing a freezing stabilizing agent including an alkali metal salt of glycerophosphoric acid in an amount sufficient to reduce damage to the cells as a result of freezing. Disodium beta glycerophosphoric acid is the preferred salt.

It has been found that the alkali metal glycerophosphate salts (GP salts) generally improve the initial lactic acid production of bacteria which have been frozen and which are thawed and used to form lactic acid in milk. Since lactic acid is a main product of the fermentation of milk in making buttermilk, cheese and cottage cheese and the like, and since shortened fermentation time reduces costs this finding is economically important. In any event, the GP salts stabilize the bacteria from damage upon freezing.

The bacteria which are stabilized by the GP salts and used as dairy or milk fermenting starters are included in the families *Streptococcaceae* and *Lactobacillaceae*, comprising the genera *Streptococcus, Leuconostoc* and *Lactobacillus*. Representative members are *Streptococcus lactis, Streptococcus cremoris, Streptococcus thermophilus, Leuconostoc spp., Lactobacillus bulgaricus, Lactobacillus acidophilus* and *Lactobacillus lactis*. These lactic acid bacteria can be combined with so called "aroma" forming bacteria of the genus *Leuconostoc*, in particular *Leuconostoc citrovorum* or *Leuconostoc dextranicum* used in making buttermilk. The classification is as defined in *Bergey's Manual*, Eighth Edition (1974). By contrast, it was found that bacteria generally not used in milk fermentations were not freeze stabilized by the GP salts.

The useful alkali metal salts of glycerophosphoric acid are principally sodium and potassium. Disodium beta glycerophosphate is particularly preferred. It has been found that these salts generally enhance the lactic acid producing capabilities of frozen bacterial compositions used as starters. By contrast, the corresponding calcium salt was found to be ineffective, probably because of its limited solubility in milk.

The alkali metal salts of glycerophosphoric acid can be used alone or preferably in admixture with glycerol or other known freezing stabilizing agents which are usually of the class of hygroscopic, di- and polyhydric alkyl alcohols, such as mannitol, containing between 3 to 6 carbon atoms and which can be used in foods. Usually between about 0.1 to 5 percent by weight salt is used based upon the volume of the bacterial concentrate. When glycerol or other stabilizing agents are used in addition, they are used in an amount between about 1 to 20 percent by volume of the concentrate.

The compositions usually contain at least about $10^9$ bacterial cells per ml. This concentration facilitates freezing and shipping and produces more effective results in use. With certain lactic acid bacteria these GP salt stabilized concentrates preferably exhibit an increase of "lactic acid activity" in milk in 3.5 hours at 37.7°C of at least about 10 percent with the addition of the GP salt by comparison to concentrates without the GP salts. Lactic acid activity is determined by the method of *Horral and Elliker, J. Dairy Sci.* Vol 33 pages 245–249 (1950$^a$).

SPECIFIC DESCRIPTION

Having generally described the present invention, the following are specific Examples.

The Horral et al method was used to determine lactic acid activity in the following examples. Tubes containing 10 ml of sterile skim milk were adjusted to 37.7°C in a constant temperature bath. Duplicate tubes were inoculated with 0.3 ml of suitable dilutions of the concentrate. After 3.5 hr, the tubes were transferred to an ice bath. The contents of each tube were rinsed with 5 ml of distilled water into a 125 ml erlenmeyer flask and the acidity was determined by titration.

The titratable acidity of a milk culture was determined by transferring 10 ml of the culture to a 125 ml erlenmeyer flask with a 10 ml serological pipette. Ten ml of distilled water, used to rinse the pipette, was added to the sample. Five drops of 1% solution of phenolphthalein in 95% ethanol was added, and the milk was titrated to the phenolphthalein end point with standarized 0.1 N NaOH. The activity of the culture was the titratable acidity calculated as percent by weight lactic acid. The acidity or activity of the sample, expressed as percent lactic acid, was calculated as follows:

$$\text{Percent Lactic acid} = \frac{(\text{ml of base}) (\text{normality of base}) (9)}{\text{ml of sample}}$$

The specific gravity of the milk or buttermilk was assumed to be 1.0.

In the following Examples, a stock solution containing 25% by weight NaGP was prepared and stored in refrigerator. The glycerol level used in all cases was 10% by volume. Both of these compounds were sterilized by autoclaving at 121°C for 15 minutes.

For 5 ml of concentrate per tube, the amount of NaGP in ml of the 25% stock solution was as follows:

| | |
|---|---|
| For 1.0% (0.05g) | 0.2 ml of stock |
| For 2.0% (0.10g) | 0.4 ml of stock |
| For 0.5% (0.025g) | 0.1 ml of stock |
| For 0.2% (0.010g) | 0.4 ml of 1/10 dilution of stock |

EXAMPLE I

Procedure: Concentrates (containing about $10^{11}$ cells per ml) of mixed *Streptococcus lactis* and *Streptococcus cremoris* cultures to be used and known to be effective for making cheese, were collected aseptically in dilution bottles as the concentrates were discharged from the centrifuge after growth in a suitable nutrient medium such as that disclosed in U.S. Reissue Pat. No. 28,276. Aliquots of the concentrates with sodium-beta-glycerophosphate (NaGP) at different concentrations, and without NaGP were distributed into sterile, plastic tubes and frozen by direct contact with dry ice in a styrofoam container. The frozen cultures were stored in −20°C deep freeze and taken out after 2 to 3 days, quickly thawed at 40°C and tested for acid producing activity.

| Tube No. | ml Concentrate | ml of stock NaGP | NaGP (weight/volume) |
|---|---|---|---|
| 1. Control A | 5.0 | — | — |
| 2. Experimental | 5.0 | 0.4 ml of 1/10 dil | 0.2 |
| 3. Experimental | 5.0 | 0.1 ml stock | 0.5 |
| 4. Experimental | 5.0 | 0.2 ml stock | 1.0 |
| 5. Experimental | 5.0 | 0.4 ml stock | 2.0 |

| Tube No. | ml 0.1 N NaOH Used | % by weight lactic acid* | |
|---|---|---|---|
| 1. Control | 6.10 | 0.55 | |
| 2. (0.2%) | 7.10 | 0.64 | The inocula in all these tubes were diluted with water 1:9 before testing (1/10th dilution) |
| 3. (0.5%) | 7.10 | 0.64 | |
| 4. (1.0%) | 7.20 | 0.65 | |
| 5. (2.0%) | 7.20 | 0.65 | |

*Horral et al test

Interpretation: It was concluded that addition of NaGP definitely stimulates acid producing activity in these bacteria and that there was stabilization even at low concentration levels. Usually at least about 4.0% by volume glycerol is required. In particular, the addition of NaGP to the concentrate just before freezing is stimulating. The magnitude of stimulation was the same over the concentration levels tried for NaGP with these bacteria.

EXAMPLE II

The object of this test was to determine if the NaGP containing concentrates can be used for direct set Chedder cheese without preparing bulk starters.

Procedure: The bacteria of Example I were inoculated into activity test tubes and were adjusted to coincide with a rate of 15 oz. per 1000 gallons of milk. This works out to 1.1 ml per 10 ml of milk of a $1 \times 10^{-3}$ aqueous dilution of the concentrate of Example I which contained about $1 \times 10^{11}$ cells per ml.

| Tube No. | ml 0.1 N NaOH Used | % by weight lactic acid |
|---|---|---|
| 1. Control | 2.5 | 0.23 |
| 2. 0.2% NaGP | 2.5 | 0.23 |
| 3. 0.5% NaGP | 2.5 | 0.23 |
| 4. 1.0% NaGP | 2.6 | 0.23 |
| 5. 2.0% NaGP | 2.6 | 0.23 |

Interpretation: The lactic acid activity is poor because of the extreme dilution of the NaGP. At least 0.4 percent lactic acid activity is needed to be satisfactory for setting milk to make cheese and thus it was concluded that there would be no enhancement of acid producing activity at this low concentration level when the concentrates were directly added to the milk. Repetition of Example II at inoculations of twice and four times produced equivalent results.

EXAMPLE III

The objective of this test was to determine if the addition of NaGP to milk at low concentration levels (rather than to the culture) will induce stimulation.

Procedure: The procedure was to add to milk the equivalent amount of NaGP available when concentrates of Example I containing 0.2% or 1.0% of NaGP are used and then determine activity with Control culture. The tests were compared against parallel tubes of Experimental concentrates. The calculations were as follows:

The level NaGP present in the original concentrate tube was 0.2%. For the 1/10 dilution used for activity test, the percentage content of NaGP was 0.02%. Each ml of 1/10 dilution contains 0.0002 g ($2 \times 10^{-4}$g) of NaGP. Each 0.3 ml inoculum contains $0.6 \times 10^{-4}$g ($6.0 \times 10^{-5}$g) of NaGP or (60 micrograms/10 ml milk). A 1% level of NaGP is equivalent to 300 micrograms/10 ml milk. A 1/1000 dilution of the 25% NaGP solution contains 0.25 m/ml (250 micrograms/ml) which is Solution A. Thus 1.20 ml of Solution A contains 300 micrograms and 0.25 ml of Solution A contains 62.5 micrograms of NaGP (approximately the level needed, namely 60 micrograms per 10 ml of milk).

| Tube No. | Description | ml NaOH | % Lactic Acid |
|---|---|---|---|
| 1. | Control at 1/10 dilution | 6.7 | 0.60 |
| 2. | Control of tube 1 plus 0.25 ml A to milk | 6.5 | 0.59 |
| 3. | Control of tube 1 plus 1.25 ml A to milk | 6.8 | 0.61 |
| 4. | 0.2% NaGP Expermimental | 7.3 | 0.66 |
| 5. | 0.5%     " | 6.9 | 0.62 |

-continued

| Tube No. | Description | ml NaOH | % Lactic Acid |
|---|---|---|---|
| 6. | 1.0% " | 7.3 | 0.66 |
| 7. | 2.0% " | 7.3 | 0.66 |
| 8. | Uninoculated control plus 300 mg Na-B-glycero-phosphate | 2.1 | 0.19 |

Interpretation: The addition of NaGP at 0.2% and 1.0% levels (at the inoculation dilution and rate used) to milk and inoculation with 0.3 ml of 1/10 dilution of control culture did not increase activity. However, the parallel experimental culture containing NaGP still retained enhanced activity. The increased acidity is not contributed by NaGP per se but by the stimulation of culture. Thus a certain level of NaGP is required to achieve stimulation.

EXAMPLE IV

The objective was to determine if the increased activity with NaGP phosphate is due to a cryoprotective effect, or due to stimulation of acid production.

Procedure: Concentrates of the mixed concentrate of Example I with about 10 percent by weight of *Leuconostoc citrovorum* added which is used in making buttermilk by direct addition to milk were frozen with and without NaGP in the presence or absence of 10% glycerol level.

Results:

| Tube No. | Description | % lactic acid | |
|---|---|---|---|
| 1. | control - no glycerol | 0.35 | |
| 2. | control - with glycerol | 0.36 | |
| 3. | 0.2% NGP alone | 0.34 | |
| 4. | 0.2% NGP + glycerol | 0.37 | (1/10th dilution) of culture was used. |
| 5. | 1.0% NGP only | 0.37 | |
| 6. | 1.0% NGP + glycerol | 0.45 | |

Interpretation: The effect is not cryoprotective alone and is at least partially due to stimulation. The stimulation was more evident at the higher levels of NaGP.

EXAMPLE V

The procedure of Example IV was repeated with a concentrate containing the same species of bacteria but of different strains.
Results:

| Tube No. | Description | % lactic acid | |
|---|---|---|---|
| 1. | control - no glycerol | 0.34 | |
| 2. | control - with glycerol | 0.35 | |
| 3. | 0.2% NGP alone | 0.35 | 1/10 dilution of culture was used |
| 4. | 0.2% NGP + glycerol | 0.39 | |
| 5. | 1.0% NGP alone | 0.42 | |
| 6. | 1% NGP + glycerol | 0.52 | |

Interpretation: It was clear that at the higher levels of NaGP alone or with glycerol there was an enhanced activity.

EXAMPLE VI

The procedure of Example I was repeated after the concentrate had been stored for one month.

| Tube No. | Description | % lactic acid | |
|---|---|---|---|
| 1. | control - no glycerol | 0.41 | |
| 2. | control - with glycerol | 0.41 | |
| 3. | 0.2% NGP | 0.47 | 1/10th dilution of culture was used |
| 4. | 0.2% NGP + glycerol | 0.44 | |
| 5. | 1.0% NGP | 0.49 | |
| 6. | 1.0% NGP + glycerol | 0.51 | |

Interpretation: As can be seen, parallel results were achieved although there is a general loss of activity for all samples as a function of time which is not unusual with some strains of lactic acid bacteria.

EXAMPLE VII

The procedure of Example IV was repeated with concentrates stored for one month.

| Tube No. | Description | % lactic acid | |
|---|---|---|---|
| 1. | control - no glycerol | 0.34 | |
| 2. | control + glycerol | 0.46 | |
| 3. | 0.2% NGP | 0.32 | 1/10 dilution of culture was used. |
| 4. | 0.2% NGP + glycerol | 0.42 | |
| 5. | 1.0% NGP | 0.36 | |
| 6. | 1.0% NGP + glycerol | 0.53 | |

Interpretation: As can be seen again, parallel results were achieved without a general loss of activity for all samples as a function of time.

The ability of the organisms to survive extended storage was determined by removing samples at monthly intervals for plating and for determining the activity. In some instances, the stored cultures also were used to prepare buttermilk. Frozen samples were quickly thawed in a water bath at 40°C and used for plating and for determinng the activity. In all instances it was found that there was enhanced acid activity resulting from the use of NaGP over a period of time for those bacteria exhibiting an improved result initially. In general it was found that the use of NaGP produced at least about a ten percent (10%) increase in acid activity over the use of glycerol alone.

It was found that certain strains of lactic acid bacteria did not show enhanced lactic acid producing activity when used with the GP salts at the levels tested. The GP salts did, however, stabilize the concentrates to freezing. It was also found that the GP salts could in addition be added in larger amounts to dry bulk starter media used for setting starters for cultured dairy products. These bulk starters could then be inoculated with the concentrates of the present invention in order to achieve the required activity of lactic acid of at least about 0.4% in the cheese milk. In the bulk starter, the amount of the GP salt is between about 0.01 and 0.5 parts by weight per part by weight of dry medium, which is reconstituted to between about 8.5% to 11% solids.

The mixture of the GP salt and the thawed frozen concentrate can be added directly to the milk and the same result achieved as with the bulk starters. The amount of concentrate added to the milk should result in the milk containing a minimum of $1 \times 10^7$ cells per ml. The amount of GP salt must be between about 0.01 to 0.5 part by weight per part by weight of milk. Thus large amounts of each ingredient are required for direct sets as compared to the use of bulk starters.

I claim:

1. A frozen bacterial composition comprising live bacterial cells of the kind which form lactic acid in milk mixed with a cell growth medium and containing a freezing stabilizing agent including an alkali metal salt of glycerophosphoric acid the salt being present in an amount sufficient to reduce damage to the cells as a result of freezing.

2. The composition of claim 1 wherein the salt is included in an amount which is sufficient to enhance the lactic acid forming characteristics of the bacteria.

3. The composition of claim 1 wherein the cells are selected from *Streptococcus lactis, Streptococcus cremoris, Streptococcus thermophilus, Lactobacillus bulgaricus, Lactobacillus acidophilus* and *Lactobacillus lactis*.

4. The composition of claim 1 which in addition contains *Leuconostoc citrovorum* or *Leuconostoc dextranicum*.

5. The composition of claim 1 which has a lactic acid activity in milk of at least about 10% measured in 3.5 hours at 37.7°C.

6. The composition of claim 1 wherein the salt is included in an amount which is sufficient to reduce the drop in viable cell count during storage when the storage is at a temperature of less than about −20°F for extended periods of time.

7. The composition of claim 1 wherein the amount of the salt is between about 0.1 to 5 percent by weight based upon a volume amount of concentrate.

8. The composition of claim 1 wherein the alkali metal is disodium beta glycerophosphate.

9. The composition of claim 1 which contains at least about $10^9$ cells per milliliter.

10. The composition of claim 1 which contains glycerol as an additional freezing stabilizing agent.

11. The composition of claim 10 wherein about 0.1 to 5 percent by weight of the salt is used based upon a volume amount of concentrate with between about 1 to 20 percent by volume glycerol as the stabilizing agent based upon the volume amount of concentrate.

12. The composition of claim 1 wherein the growth medium includes milk.

13. The method for enhancing the lactic acid producing activity of bacteria in making cultured dairy products which comprises:
   a. providing a concentrate which has been frozen and then thawed for use comprising live bacterial cells which form lactic acid in milk mixed with a cell growth medium and containing a freezing stabilizing agent added after concentration of the cells including an alkali metal salt of glycerophosphoric acid in an amount sufficient to reduce damage to the cells as a result of freezing; and
   b. mixing the thawed concentrate with a bulk starter medium containing an additional amount of salt of glycerophosphoric acid and water.

14. The method of claim 13 wherein the bulk starter medium is composed of milk or derivatives of milk.

15. The method of claim 14 wherein the bulk starter medium contains between about 0.01 and 0.5 parts of the alkali metal salt of glycerophosphoric acid per part of dry medium, which is reconstituted to about 8.5% to 11% solids.

16. The method of claim 15 wherein the salt is disodium beta glycerophosphoric acid.

17. The method for enhancing the lactic acid producing activity of bacteria in making cultured dairy products which comprises:
   a. providing a concentrate which has been frozen and thawed for use comprising live bacterial cells which form lactic acid in milk mixed with a cell growth medium and containing a freezing stabilizing agent added after concentration of the cells including an alkali metal salt of glycerophosphoric acid in an amount sufficient to reduce damage to the cells as a result of freezing; and
   b. mixing the thawed concentrate with milk to be cultured along with an additional amount of the salt of glycerophosphoric acid in an amount sufficient to cause stimulation of the lactic acid activity of the bacteria because of the salt so as to produce the cultured dairy product.

18. The method of claim 17 wherein the salt is disodium beta glycerophosphate.

19. The method of claim 17 wherein the milk after the addition of the concentrate and salt contains at least about $1 \times 10^7$ cells per ml of milk and about 0.01 to 0.5 parts by weight of the salt per part by weight of milk.

* * * * *

UNITED STATES PATENT OFFICE
CERTIFICATE OF CORRECTION

PATENT NO. : 3,975,545
DATED : August 17, 1976
INVENTOR(S) : Ebenezer R. Vedamuthu It is certified that error appears in the above-identified patent and that said Letters Patent are hereby corrected as shown below:

Column 3, line 60, "Chedder" should be --Cheddar--.

Column 6, line 49, "determinng" should be --determining--.

Claim 17, line 30 after "and" insert --then--.

Signed and Sealed this

Fourteenth Day of December 1976

[SEAL]

Attest:

RUTH C. MASON
*Attesting Officer*

C. MARSHALL DANN
*Commissioner of Patents and Trademarks*